US012570598B2

(12) United States Patent
Suzuki et al.

(10) Patent No.:  US 12,570,598 B2
(45) Date of Patent:  Mar. 10, 2026

(54) METHOD FOR PRODUCING ISOBUTYLENE, METHOD FOR PRODUCING METHACRYLIC ACID, AND METHOD FOR PRODUCING METHYL METHACRYLATE

(71) Applicant: Mitsubishi Chemical Corporation, Tokyo (JP)

(72) Inventors: Tatsuya Suzuki, Tokyo (JP); Yuuki Katou, Tokyo (JP); Wataru Ninomiya, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 804 days.

(21) Appl. No.: 17/932,441

(22) Filed: Sep. 15, 2022

(65) Prior Publication Data

US 2023/0027797 A1      Jan. 26, 2023

Related U.S. Application Data

(63) Continuation of application No. PCT/JP2021/013218, filed on Mar. 29, 2021.

(30) Foreign Application Priority Data

Mar. 31, 2020    (JP) ................................. 2020-064207

(51) Int. Cl.
*C07C 67/08* (2006.01)
*B01J 21/04* (2006.01)
(Continued)

(52) U.S. Cl.
CPC .............. *C07C 67/08* (2013.01); *B01J 21/04* (2013.01); *B01J 35/40* (2024.01); *B01J 35/50* (2024.01);
(Continued)

(58) Field of Classification Search
None
See application file for complete search history.

(56) References Cited

U.S. PATENT DOCUMENTS

| | | | |
|---|---|---|---|
| 9,079,813 B2 | 7/2015 | Adam et al. | |
| 2005/0014985 A1* | 1/2005 | Grund ....................... | C07C 1/24 |
| | | | 422/600 |
| 2013/0204058 A1 | 8/2013 | Adam et al. | |
| 2013/0289298 A1 | 10/2013 | Tateno et al. | |
| 2014/0357890 A1 | 12/2014 | Ooyachi et al. | |
| 2015/0239801 A1 | 8/2015 | Adam et al. | |

(Continued)

FOREIGN PATENT DOCUMENTS

| | | |
|---|---|---|
| CN | 106458786 A | 2/2017 |
| CN | 106470963 A | 3/2017 |

(Continued)

OTHER PUBLICATIONS

Korean Office Action issued Apr. 22, 2024 in Korean Application No. 10-2022-7032097 with English Machine translation, 10 pgs.

(Continued)

*Primary Examiner* — Amy C Bonaparte
(74) *Attorney, Agent, or Firm* — Oblon, McClelland, Maier & Neustadt, L.L.P.

(57) ABSTRACT

There is provided a method for producing isobutylene, in which isobutylene is produced from isobutanol with a high selectivity while suppressing a decrease in the isobutanol conversion rate under pressure. In the method for producing isobutylene according to the present invention, a raw material gas containing isobutanol is brought into contact with a catalyst to produce isobutylene from isobutanol, the method including bringing the raw material gas containing isobutanol into contact with a catalyst at a linear velocity of 1.20 cm/s or more under a pressure of 120 kPa or more in terms of absolute pressure to produce isobutylene from isobutanol.

7 Claims, 4 Drawing Sheets

(51) Int. Cl.

| | |
|---|---|
| *B01J 35/40* | (2024.01) |
| *B01J 35/50* | (2024.01) |
| *C07C 1/24* | (2006.01) |
| *C07C 29/04* | (2006.01) |
| *C07C 51/235* | (2006.01) |
| *C07C 51/25* | (2006.01) |

(52) U.S. Cl.
CPC ................ *C07C 1/24* (2013.01); *C07C 29/04* (2013.01); *C07C 51/235* (2013.01); *C07C 51/25* (2013.01); *C07C 51/252* (2013.01); *B01J 2235/00* (2024.01); *C07C 2521/04* (2013.01)

(56) References Cited

U.S. PATENT DOCUMENTS

| | | | |
|---|---|---|---|
| 2016/0304432 A1* | 10/2016 | Bos | ............................ C07C 5/48 |
| 2017/0050896 A1 | 2/2017 | Yasukawa et al. | |
| 2017/0129844 A1 | 5/2017 | Akihara et al. | |
| 2018/0072636 A1 | 3/2018 | Suzuki et al. | |

FOREIGN PATENT DOCUMENTS

| | | |
|---|---|---|
| CN | 107118069 A | 9/2017 |
| CN | 107405601 A | 11/2017 |
| JP | 47-14068 | 8/1972 |
| JP | 2012-219042 A | 11/2012 |
| JP | 2013-121946 A | 6/2013 |
| WO | WO 2012/016785 A1 | 2/2012 |
| WO | WO 2012/096367 A1 | 7/2012 |
| WO | WO 2013/069630 A1 | 5/2013 |
| WO | WO 2015/170686 A1 | 11/2015 |
| WO | WO 2016/002649 A1 | 1/2016 |

OTHER PUBLICATIONS

Combined Chinese Office Action and Search Report issued Sep. 25, 2023 in Chinese Patent Application No. 202180014928.3 (with English Translation), 23 pages.

Combined Brazilian Office Action and Search Report issued Mar. 12, 2024 in Brazilian Patent Application No. BR112022017268-0 (with English translation), 10 pages.

Saudi Arabian Office Action issued Dec. 10, 2023 in Saudi Arabian Patent Application No. 522440674 (with English translation), 8 pages.

Indonesian Office Action issued Dec. 12, 2023 in Indonesian Patent Application No. P00202210546 (with English translation), 6 pages.

Extended European Search Report issued Aug. 28, 2023 in European Patent Application No. 21778952.8, 9 pages.

Indian Hearing Notice issued Sep. 6, 2023 in Indian Patent Application No. 202247056205, 2 pages.

Saudi Arabian Office Action issued Mar. 29, 2023 in Saudi Arabian Patent Application No. 522440674, 12 pages.

Japanese Office Action issued Apr. 18, 2023 in Japanese Patent Application No. 2022-512192 (with unedited computer-generated English Translation), 6 pages.

Indian Office Action issued Dec. 14, 2022 in Indian Patent Application No. 202247056205, 6 pages.

Chinese Office Action issued Jun. 6, 2024 in Chinese Patent Application No. 202180014928.3 (with English translation), 23 pages.

International Search Report issued May 25, 2021 in PCT/JP2021/013218, filed on Mar. 29, 2021, 3 pages.

Arnby, K et al., Characterization of Pt/$\gamma$-Al$_2$O$_3$ catalysts deactivated by hexamethyldisiloxane, Applied Catalysis B: Environmental, 2004, vol. 54, 8 Pages.

Chaplits, et al., "Dehydration of Tertiary Butyl Alcohol in a Reactor of a New Design", Khimicheskaya Promyshlennost, vol. 42, No. 10, 1966, 1 Page.

Banzaraktsaeva, et al., "Ethanol-to-Ethylene Dehydration on Acid-Modified Ring-Shaped Alumina Catalyst in a Tubular Reactor", Chemical Engineering Journal, 2019, vol. 374, 14 Pages.

Office Action issued Feb. 19, 2024, in corresponding Singaporean Patent Application No. 11202253583C, 7 pages.

Chinese Office Action issued Apr. 11, 2024 in Chinese Patent Application No. 202180014928.3 (with unedited computer-generated English translation), 14 pages.

* cited by examiner

METHOD FOR PRODUCING ISOBUTYLENE, METHOD FOR PRODUCING METHACRYLIC ACID, AND METHOD FOR PRODUCING METHYL METHACRYLATE

This application is a continuation application of International Application No. PCT/JP2021/013218, filed on Mar. 29, 2021, which claims the benefit of priority of the prior Japanese Patent Application No. 2020-064207 filed in Japan on Mar. 31, 2020, the entire contents of which are incorporated herein by reference.

TECHNICAL FIELD

The present invention relates to a method for producing isobutylene, a method for producing methacrylic acid, and a method for producing methyl methacrylate.

BACKGROUND ART

Isobutylene is one of the important raw materials of chemicals, which is converted to ethyl tert-butyl ether, paraxylene, methyl methacrylate, and the like. For example, isobutylene or tert-butyl alcohol obtained by hydrating isobutylene is subjected to the gas phase contact oxidation to obtain methacrylic acid, and then the obtained methacrylic acid is subjected to esterification with methanol, whereby methyl methacrylate can be obtained.

As a method for producing isobutylene, for example, it is known a method in which isobutanol is brought into contact with a catalyst such as alumina under pressure to dehydrate isobutanol to produce isobutylene (for example, Patent Document 1).

CITATION LIST

Patent Document

[Patent Document 1]
PCT International Publication No. WO2015/170686

SUMMARY OF INVENTION

Technical Problem

In order to industrially produce isobutylene by dehydration of isobutanol, it is desirable to react isobutanol with a high conversion rate to produce isobutylene with a high selectivity.

However, it has been found that although the dehydration of isobutanol under pressure may improve the isobutylene selectivity, the isobutanol conversion rate tends to decrease.

Therefore, an object of the present invention is to provide a method for producing isobutylene, in which isobutylene is produced from isobutanol with a high selectivity while suppressing a decrease in the isobutanol conversion rate under pressure, as well as a method for producing methacrylic acid using the method for producing isobutylene and a method for producing methyl methacrylate.

Solution to Problem

The present invention has the following aspects.

[1] A method for producing isobutylene, in which a raw material gas containing isobutanol is brought into contact with a catalyst to produce isobutylene from isobutanol, the method including bringing the raw material gas containing isobutanol into contact with a catalyst at a linear velocity of 1.20 cm/s or more under a pressure of 120 kPa or more in terms of absolute pressure to produce isobutylene from isobutanol.

[2] The method for producing isobutylene according to [1], in which a concentration of the isobutanol contained in the raw material gas containing isobutanol is 15% by volume or more and 100% by volume or less.

[3] The method for producing isobutylene according to [1] or [2], in which the catalyst has a particle diameter of 700 μm or more and 10,000 μm or less.

[4] The method for producing isobutylene according to any one of [1] to [3], in which the catalyst is a catalyst containing alumina.

[5] A method for producing methacrylic acid, including producing isobutylene according to the method for producing isobutylene according to any one of [1] to [4], and producing methacrylic acid from the obtained isobutylene.

[6] A method for producing methacrylic acid, including producing isobutylene according to the method for producing isobutylene according to any one of [1] to [4], obtaining tert-butyl alcohol from the isobutylene, and subsequently producing methacrylic acid from the obtained tert-butyl alcohol.

[7] A method for producing methyl methacrylate, including producing methacrylic acid according to the method for producing methacrylic acid according to [5] or [6], and producing methyl methacrylate from the obtained methacrylic acid and methanol.

Advantageous Effects of Invention

According to the present invention, it is possible to provide a method for producing isobutylene, in which isobutylene is produced from isobutanol with a high selectivity while suppressing a decrease in the isobutanol conversion rate under pressure. In addition, according to the present invention, it is possible to provide a method for producing methacrylic acid, in which the method for producing isobutylene according to the present invention is used, and a method for producing methyl methacrylate.

DESCRIPTION OF EMBODIMENTS

[Method for Producing Isobutylene]

Figure 1:
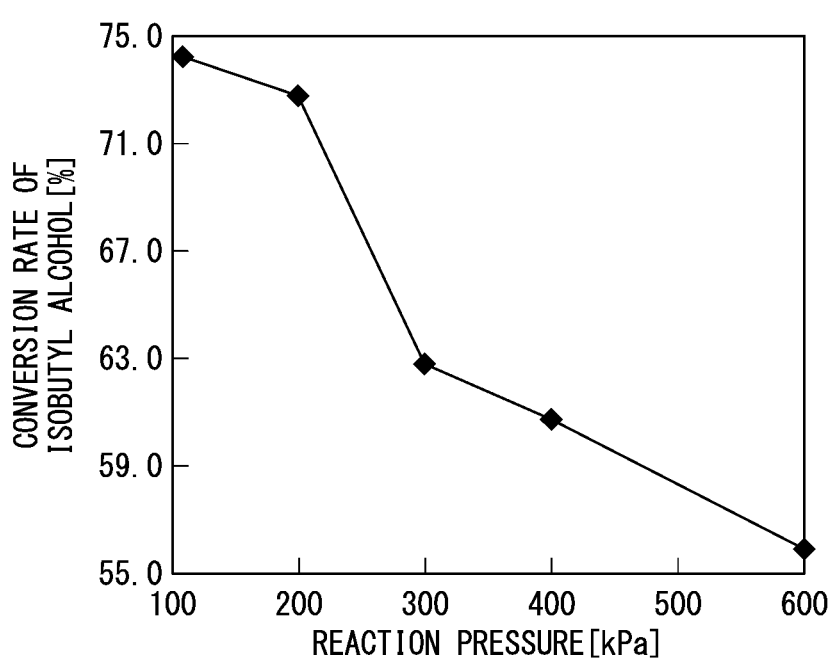
FIG. 1 is a graph showing the measurement results of the isobutanol conversion rate in the reference example.

In a method for producing isobutylene according to the present invention, isobutylene is produced from isobutanol by bringing a raw material gas containing isobutanol into contact with a catalyst. For example, by supplying a raw material gas containing isobutanol to a reactor filled with a catalyst to form a catalyst layer, the raw material gas containing isobutanol can be brought to contact with the catalyst. The type of the dehydration of isobutanol is not particularly limited, and for example, a fixed bed or a fluidized bed can be adopted.

In the present invention, a raw material gas containing isobutanol is brought into contact with a catalyst at a linear velocity of 1.20 cm/s or more, and isobutanol is dehydrated under a pressure of 120 kPa or more in terms of absolute pressure. This makes it possible to produce isobutylene with a high selectivity while suppressing a decrease in the isobutanol conversion rate under pressure.

In the present invention, the cause for capable of producing isobutylene with a high selectivity while suppressing a decrease in the conversion rate under pressure is conceived as follows.

In a case of dehydrating isobutanol under a pressure of 120 kPa or more, the isobutanol conversion rate tends to decrease although the isobutylene selectivity increases. This is conceived to be because when the raw material gas containing isobutanol is brought into contact with the catalyst under pressure, the raw material gas that is used in the present invention is difficult to come into contact with the catalyst due to the influence of the boundary film on the surface of the catalyst.

On the other hand, by setting the linear velocity of the raw material gas to 1.20 cm/s or more, it is conceived that when the raw material gas is brought into contact with the catalyst, it is difficult to be affected by the boundary film on the surface of the catalyst, and the isobutanol conversion rate is improved.

The linear velocity of the raw material gas to be brought into contact with the catalyst is 1.20 cm/s or more, preferably 1.40 cm/s or more, more preferably 1.60 cm/s or more, still more preferably 1.80 cm/s or more, even still more preferably 2.00 cm/s or more, particularly preferably 2.20 cm/s or more, and most preferably 2.40 cm/s or more. When the linear velocity of the raw material gas is equal to or higher than the above-described lower limit value, the decrease in the isobutanol conversion rate under pressure can be suppressed, and the isobutylene selectivity is improved.

On the other hand, for the above-described reason, the conversion rate tends to be improved when the linear velocity of the raw material gas is equal to or higher than the above-described lower limit value, and thus the upper limit value of the linear velocity is not particularly limited. For example, the linear velocity of the raw material gas can be 5,000 cm/s or less.

The pressure in the dehydration of isobutanol is 120 kPa or more, preferably 150 kPa or more, more preferably 170 kPa or more, still more preferably 190 kPa or more, and particularly preferably 210 kPa or more, in terms of absolute pressure. It is especially preferably 230 kPa or more. When the pressure in the dehydration is equal to or higher than the above-described lower limit value, the isobutylene selectivity is improved. The pressure in the dehydration of isobutanol is preferably 100,000 kPa or less, more preferably 50,000 kPa or less, still more preferably 10,000 kPa or less, even still more preferably 5,000 kPa or less, particularly preferably 2,500 kPa or less, and most preferably 1,000 kPa or less. The above-described upper and lower limits may be combined in any combination. For example, the pressure in the dehydration of isobutanol is preferably 120 kPa or more and 100,000 kPa or less, more preferably 150 kPa or more and 50,000 kPa or less, still more preferably 170 kPa or more and 10,000 kPa or less, even still more preferably 190 kPa or more and 5,000 kPa or less, even further still more particularly preferably 210 kPa or more and 2,500 kPa or less, and particularly preferably 230 kPa or more and 1,000 kPa or less.

When the pressure in the dehydration of isobutanol is equal to or lower than the above upper limit, the supply amount of isobutanol, which is required to increase the linear velocity of the raw material gas to be brought into contact with the catalyst to 1.20 cm/s or more, can be reduced, and the process enlargement can be prevented.

The pressure in the dehydration is a value measured by a pressure sensor installed at a position where the influence of the pressure loss can be ignored with respect to the pressure at the inlet of the reactor.

The reaction temperature in the dehydration of isobutanol is preferably 390° C. or lower, more preferably 380° C. or lower, still more preferably 370° C. or lower, particularly preferably 360° C. or lower, and most preferably 350° C. or lower. When the reaction temperature is equal to or lower than the above-described range of the upper limit value, the isomerization reaction is easily suppressed and the selectivity for isobutylene is improved.

The reaction temperature in the dehydration of isobutanol is preferably 240° C. or higher, more preferably 250° C. or higher, still more preferably 260° C. or higher, particularly preferably 270° C. or higher, and most preferably 280° C. or higher. When the reaction temperature is equal to or higher than the above-described range of the lower limit value, the using amount of the catalyst and the supply amount of the raw material gas can be reduced, which is advantageous in terms of cost and productivity.

The above-described upper and lower limits may be combined in any combination. For example, the reaction temperature in the dehydration of isobutanol is preferably 240° C. or higher and 390° C. or lower, more preferably 250° C. or higher and 380° C. or lower, still more preferably 260° C. or higher and 370° C. or lower, even still more preferably 270° C. or higher and 360° C. or lower, and particularly preferably 280° C. or higher and 350° C. or lower.

The lowest temperature, among the temperatures of the catalyst layer in the reactor, which can be confirmed after the reaction reached a steady state is defined as the reaction temperature. Therefore, when the temperature of the catalyst layer varies, it is preferable to increase the number of measurement points or measure the temperature continuously in the catalyst filling direction. The method for controlling the reaction temperature is not particularly limited, and a known method can be adopted.

The isobutanol that is used as a starting raw material is not particularly limited, and it may be biomass-derived isobutanol from the viewpoint of environmental protection.

The "biomass-derived isobutanol" is either isobutanol purified from an organic compound obtained by using fermentable sugar of biomass and subjecting it to a fermentation process or isobutanol obtained by a process including any one or more processes of catalytic chemical conversion and thermochemical conversion of biomass.

The biomass can be broadly divided into one derived from resource crops and one derived from waste. Examples of the biomass derived from resource crops include food crops, wood, and flowers, and unused portions of these crops can also be used. Examples of the biomass derived from waste include food waste, sludge such as sewage, livestock excreta, and waste paper.

For example, by vaporizing a raw material with a vaporizer, it can be supplied to a reactor as a raw material gas. The vaporizer is not particularly limited, and examples thereof include a jacket type, a horizontal tube type with a natural circulation system, an immersion tube type with a natural circulation system, a vertical short tube type with a natural circulation system, a rising membrane type having a vertical long tube, a descending membrane type having a horizontal tube, a horizontal tube type with a forced circulation system, a vertical tube type with a forced circulation system, and a coil type.

In the raw material gas, the isobutanol concentration can be adjusted by diluting isobutanol with a diluent gas. The raw material gas may be a gas consisting only of isobutanol.

The diluent gas may be any gas that does not affect the dehydration of isobutanol, and examples thereof include nitrogen, helium, neon, krypton, xenon, radon, argon, methane, ethane, propane, butane, isobutane, carbon monoxide, carbon dioxide, nitric oxide, nitrogen dioxide, nitrous oxide, dinitrogen trioxide, dinitrogen tetroxide, dinitrogen pentoxide, and water vapor. Oxygen or hydrogen may be used as a diluent gas as long as it does not affect the dehydration of isobutanol. The diluent gas included in the raw material gas may be one kind or two or more kinds. moisture may be included in the raw material gas.

The isobutanol concentration in the raw material gas is preferably 15.0% by volume or more, more preferably 20% by volume or more, still more preferably 30% by volume or more, particularly preferably 40% by volume or more, even still more preferably 50% by volume or more, and most preferably 55% by volume or more, with respect to the total volume of the raw material gas.

When the isobutanol concentration is equal to or larger than the above-described lower limit value, the isomerization reaction is easily suppressed and thus the isobutylene selectivity is improved. In addition, the reactor can be easily miniaturized, the equipment cost can be reduced, and the energy cost required for the recovery of isobutylene can be reduced. The upper limit is not particularly limited, and it is 100% by volume or less.

The catalyst to be used in the dehydration of isobutanol is not particularly limited as long as it is a catalyst capable of dehydrating isobutanol, and examples thereof include dehydration catalysts, among which an acid catalyst is preferable.

Examples of the acid catalyst include alumina, silica alumina, zeolite, solid phosphoric acid, and titania. The catalyst preferably contains alumina from the viewpoint that the isobutylene selectivity is high.

In the present invention, the alumina catalyst means a catalyst in which the proportion of alumina to the total mass of the catalyst is 90% by mass or more. One kind of catalyst may be used singly, or two or more kinds thereof may be used in combination.

The crystal form of alumina that is used in the present invention is not particularly limited. Examples thereof include α-alumina, β-alumina, γ-alumina, σ-alumina, θ-alumina, δ-alumina, and alumina hydrate. In particular, a catalyst containing γ-alumina is preferable from the viewpoint of activity and selectivity. Alumina in these crystal forms may be used alone or in a combination of two or more thereof.

When two or more kinds thereof are used in combination, those having crystal forms different from each other may be used, or a crystal state of a mixed phase may be taken.

The alumina that is used in the catalyst according to the present invention can be easily produced by a known method including, for example, a thermal decomposition method, a precipitation method, a deposition method, a kneading method, or a method in which these methods are used in combination. Examples of the raw material for alumina include a material that generates alumina or alumina hydrate by heating or hydrolysis, such as a nitrate, an acetate, an alkoxide, a sulfate, a chloride, an alkali aluminate, or alum. Examples of the alkali that is used in hydrolysis include caustic alkali, alkaline carbonate, aqueous ammonia, and ammonium carbonate.

The alumina that is used in the catalyst according to the present invention may be molded and used as necessary.

The alumina catalyst that is used in the present invention may contain a compound other than the alumina. From the viewpoint that the isobutylene selectivity is high, the content of alumina in the catalyst is preferably 95.0% by mass or more, more preferably 97.0% by mass or more, still more preferably 98.0% by mass or more, particularly preferably 99.0% by mass or more, and most preferably 99.5% by mass or more, with respect to the total mass of the alumina catalyst.

Examples of the compound other than the alumina include $SiO_2$ and $Na_2O$.

The content of $SiO_2$ in the alumina catalyst is preferably 1.0% by mass or less, more preferably 0.75% by mass or less, still more preferably 0.50% by mass or less, even still more preferably 0.40% by mass or less, even further still more preferably 0.30% by mass or less, and particularly preferably 0.20% by mass or less, with respect to the total mass of the alumina catalyst. $SiO_2$ may not be contained in alumina.

The content of $Na_2O$ in the alumina catalyst is preferably 0.20% by mass or less, more preferably 0.15% by mass or less, still more preferably 0.10% by mass or less, even still preferably 0.075% by mass or less, even still more preferably 0.050% by mass or less, and particularly preferably 0.025% by mass or less, with respect to the total mass of the alumina catalyst. $Na_2O$ may not be contained in alumina.

The contents of alumina, $SiO_2$, and $Na_2O$ in the catalyst are measured by an ICP emission spectroscopic analysis (ICP-AES). For example, they can be measured by Optima 8300 ICP-OES Spectrometer manufactured by Perkin Elmer, Inc.

From the viewpoint that sufficient activity can be easily obtained, the BET specific surface area of the catalyst is preferably 40.0 $m^2/g$ or more, more preferably 50.0 $m^2/g$ or more, still more preferably 60.0 $m^2/g$ or more, particularly preferably 70.0 $m^2/g$ or more, and most preferably 80.0 $m^2/g$ or more. The upper limit of the BET specific surface area of alumina is not particularly limited; however, it is preferably 350 $m^2/g$ or less.

The BET specific surface area of the catalyst is a value calculated from an $N_2$ adsorption/desorption isotherm, and it can be measured using, for example, Tristar 3000 (product name, manufactured by Shimadzu Corporation).

The size of the catalyst particle is preferably 700 μm or more and 10,000 μm or less, more preferably 800 μm or more and 9,500 μm or less, and most preferably 1,000 μm or more and 9,000 μm or less.

The particle diameter of the catalyst is defined as the size of the mesh opening of the sieve when the particles are sized with a sieve or the like. Further, in the case of a molded catalyst, for example, in a case of a columnar pellet shape, the diameter is defined as the particle diameter. When the particle diameter is too small, the pressure loss in the layer of the catalyst with which the reactor is filled becomes large, and the equipment cost and energy cost for circulating the reaction gas increase. Further, when the particle diameter is too large, the catalyst effective coefficient becomes small, which results in a decrease in activity per catalyst mass, and the isobutylene selectivity decreases.

[Method for Producing Methacrylic Acid]

The method for producing methacrylic acid according to the present invention is a method of producing methacrylic acid using isobutylene produced according to the method for producing isobutylene according to the present invention. Examples thereof include the following method (A) and method (B). According to the method (A) and the method (B), methacrylic acid can be produced from isobutylene with a high selectivity.

The method (A) includes a step (a1) of producing isobutylene according to the method for producing isobutylene according to the present invention and a step (a2) of producing methacrylic acid according to the gas phase oxidation of isobutylene.

The method (B) includes a step (b) of producing isobutylene according to the method for producing isobutylene according to the present invention, a step (b2) of hydrating isobutylene to produce tert-butyl alcohol, and a step (b3) of producing methacrylic acid according to the gas phase oxidation of the tert-butyl alcohol produced by hydrating isobutylene.

The hydration of isobutylene in the step (b2) can be carried out by a known method. Examples of the acid catalyst that is used in the hydration of isobutylene include an ion exchange resin and a heteropolyacid. The acid catalyst is preferably a strongly acidic cation exchange resin from the viewpoint that tert-butyl alcohol can be produced in a high yield.

The gas phase oxidation of isobutylene in the step (a2) or the gas phase oxidation of the tert-butyl alcohol in the step (b3) may be carried out in one stage or in two stages. Two-stage gas phase oxidation is preferable from the viewpoint of the high methacrylic acid selectivity.

When the gas phase oxidation is carried out in two stages, it is preferable to use a catalyst for the first stage oxidation in the gas phase oxidation of the first stage (the first stage oxidation). The catalyst to be used may be a known catalyst. It is preferably a catalyst containing at least molybdenum and bismuth.

Such a catalyst is preferably a catalyst having a composition represented by Formula (1).

$$Mo_{12}Bi_{a1}Fe_{a2}M_{a3}X_{a4}Y_{a5}Z_{a6}O_{a7} \qquad (1)$$

However, in Formula (1), Mo, Bi, Fe, and O each represent molybdenum, bismuth, iron, and oxygen. M represents at least one element selected from the group consisting of cobalt and nickel. X represents at least one element selected from the group consisting of chromium, lead, manganese, calcium, magnesium, niobium, silver, barium, tin, tantalum, and zinc. Y represents at least one element selected from the group consisting of phosphorus, boron, sulfur, selenium, tellurium, cerium, tungsten, antimony, and titanium. Z represents at least one element selected from the group consisting of lithium, sodium, potassium, rubidium, cesium, and thallium. a1 to a7 represent the atomic ratio of each element, a1, a2, a3, a4, a5, a6, and a7 each indicate the atomic ratio of each element to the Mo12 atom, where they are a1=0.01 to 3, a2=0.01 to 5, a3=1.0 to 12, a4=0 to 8.0, a5=0 to 5.0, and a6=0.001 to 2.0, and a7 is the atomic ratio of oxygen, which is required to satisfy the valence of each element.

The first stage oxidation can be carried out on a fixed bed. The aspect of the catalyst layer for the first stage oxidation is not particularly limited, and it may be an undiluted layer containing only the catalyst for the first stage oxidation or may be a diluted layer containing an inert carrier. The catalyst layer for the first stage oxidation may be a single layer or may be a mixed layer composed of a plurality of layers.

The concentration of isobutylene or tert-butyl alcohol in the raw material gas for the first stage oxidation is preferably 1.0% by volume or more and more preferably 3.0% by volume or more. The concentration of isobutylene or tert-butyl alcohol in the raw material gas for the first stage oxidation is preferably 20.0% by volume or less and more preferably 10.0% by volume or less.

The above-described upper and lower limits may be combined in any combination. For example, the concentration of isobutylene or tert-butyl alcohol in the raw material gas for the first stage oxidation is preferably 1.0% by volume or more and 20.0% by volume or less, more preferably 3.0% by volume or more and 20.0% by volume or less, and still more preferably 3.0% by volume or more and 10.0% by volume or less.

Although it is economical to use air as the molecular oxygen source for the first stage oxidation, it is also possible to use air enriched with pure oxygen, as necessary. The molar ratio (the volume ratio) of isobutylene or tert-butyl alcohol in a reaction gas to molecular oxygen is preferably in a range of "isobutylene or tert-butyl alcohol":"molecular oxygen"=1:0.1 to 1:5 and more preferably in a range of 0.5 to 1:3.

It is economical to use a reaction gas by diluting it with an inert gas such as nitrogen or carbon dioxide gas, water vapor, or the like, in addition to isobutylene or tert-butyl alcohol and molecular oxygen.

The reaction temperature for the first stage oxidation is preferably 200° C. or higher and 450° C. or lower, and more preferably 250° C. or higher and 400° C. or lower.

The contact time between isobutylene and molecular oxygen in the first stage oxidation is preferably 0.5 seconds or more and more preferably 1.0 seconds or more The contact time between isobutylene and molecular oxygen in the first stage oxidation is preferably 10.0 seconds or less and more preferably 6.0 seconds or less. The above-described upper and lower limits may be combined in any combination. For example, the contact time between isobutylene and molecular oxygen in the first stage oxidation is preferably 0.5 seconds or more and 10.0 seconds or less, more preferably 0.5 seconds or more and 6.0 seconds or less, and still more preferably 1.0 seconds or more and 6.0 seconds or less.

Methacrolein and methacrylic acid is obtained by the first stage oxidation. Methacrolein is converted to methacrylic acid by the gas phase oxidation of the second stage (the second stage oxidation).

A known catalyst can be used as the catalyst for the second stage oxidation, which is used in the second stage oxidation. The catalyst to be used is preferably a catalyst containing at least molybdenum and phosphorus.

Such a catalyst is preferably a catalyst having a composition represented by Formula (2).

$$P_{a8}Mo_{a9}V_{a10}Cu_{a11}A_{a12}E_{a13}Ga_{14}O_{a15} \qquad (2)$$

In Formula (2), P, Mo, V, Cu, and O each represent phosphorus, molybdenum, vanadium, copper, and oxygen. A represents at least one element selected from the group consisting of antimony, bismuth, arsenic, germanium, zirconium, tellurium, silver, selenium, silicon, tungsten, and boron. E represents at least one element selected from the group consisting of potassium, rubidium, cesium, thallium, magnesium, and barium. G represents at least one element selected from the group consisting of iron, zinc, chromium, calcium, strontium, tantalum, cobalt, nickel, manganese, titanium, tin, lead, niobium, indium, sulfur, palladium, gallium, cerium, and lanthanum. a8 to a15 represent the atomic ratio of each element. When a9=12, they are each a8=0.5 to 3, a10=0.01 to 3, a11=0.01 to 2, a12=0 to 3, preferably 0.01 to 3, a13=0.01 to 3, a14=0 to 4, and a15 is the atomic ratio of oxygen, which is required to satisfy the valence of each element.

The second stage oxidation can be carried out on a fixed bed. The catalyst layer for the second stage oxidation is not particularly limited, and it may be an undiluted layer containing only the catalyst for the second stage oxidation or may be a diluted layer containing an inert carrier. The catalyst layer for the second stage oxidation may be a single layer or may be a mixed layer composed of a plurality of layers.

The concentration of methacrolein in the reaction gas of the second stage oxidation is not limited and can be set to any concentration; however, it is preferably 1.0% by volume or more and more preferably 3.0% by volume or more. In addition, the concentration of methacrolein in the reaction gas of the second stage oxidation is preferably 20.0% by volume or less and more preferably 10.0% by volume or less. The above-described upper and lower limits may be combined in any combination. For example, the concentration of methacrolein in the reaction gas of the second stage oxidation is preferably 1.0% by volume or more and 20.0% by volume or less, more preferably 1.0% by volume or more and 10.0% by volume or less, and still more preferably 3.0% by volume or more and 10.0% by volume or less.

Although it is economical to use air as the molecular oxygen source for the second stage oxidation, it is also possible to use air enriched with pure oxygen, as necessary. The concentration of molecular oxygen in the reaction gas of the second stage oxidation is preferably 0.5 mol or more and more preferably 1.0 mol or more with respect to 1.0 mol of methacrolein. In addition, the molecular oxygen concentration in the reaction gas of the second stage oxidation is preferably 4.0 mol or less and more preferably 3.0 mol or less with respect to 1.0 mol of methacrolein. The above-described upper and lower limits may be combined in any combination. For example, the concentration of molecular oxygen in the second stage oxidation is preferably 0.5 mol or more and 4.0 mol or less, more preferably 1.0 mol or more and 4.0 mol or less, and still more preferably 1.0 mol or more and 3.0 mol or less with respect to 1.0 mol of methacrolein.

To the reaction gas for the second stage oxidation, water (water vapor) may be added in addition to methacrolein and molecular oxygen.

Although the reaction gas for the second stage oxidation may contain a small amount of impurities such as lower saturated aldehyde, the amount thereof is preferably as small as possible. Further, the reaction gas for the second stage oxidation may contain an inert gas such as nitrogen gas or carbon dioxide gas.

The reaction pressure for the second stage oxidation can be set in a range from atmospheric pressure to several hundred kPaG. The reaction temperature for the second stage oxidation is preferably 230° C. or higher and more preferably 250° C. or higher. In addition, the reaction temperature for the second stage oxidation is preferably 450° C. or lower and more preferably 400° C. or lower. The above-described upper and lower limits may be combined in any combination. For example, the reaction temperature for the second stage oxidation is preferably 230° C. or higher and 400° C. or lower, more preferably 250° C. or higher and 450° C. or lower, and still more preferably 250° C. or higher and 400° C. or lower.

[Manufacturing Method for Methyl Methacrylate]

The method for producing methyl methacrylate according to the present invention is a method of producing methyl methacrylate using the methacrylic acid of the present invention.

The method for producing methyl methacrylate according to the present invention includes a step of producing the methacrylic acid according to the present invention and a step of subjecting the methacrylic acid to esterification with methanol. According to the method according to the present invention, methyl methacrylate can be produced from isobutylene with a high selectivity.

For example, methacrylic acid produced according to the production method according to the present invention is recovered by extraction, distillation operation, or the like, and it is subjected to esterification with methanol in the presence of an acid catalyst.

It is preferable to use a catalyst for esterification. The catalyst to be used is preferably an acid catalyst, and for example, sulfuric acid or an ion exchange resin can be used. The ion exchange resin is preferably a strongly acidic cation exchange resin. Specific examples of the strongly acidic cation exchange resin include DIAION (registered trade name), PK216, RCP12H (manufactured by Mitsubishi Chemical Corporation), LEWATIT (registered trade name), K2431 (manufactured by Bayer AG), and Amberlyst (registered trade name) 15WET (manufactured by Rohm and Haas Company, Japan). These may be used alone or in a combination of two or more thereof.

The flow direction of the reaction fluid in esterification may be either vertically upward or vertically downward, and it can be appropriately selected. When the swelling of the ion exchange resin that is used as the acid catalyst for esterification is large, the flow direction of the reaction fluid is preferably vertically upward. When the reaction fluid forms a non-uniform phase, the flow direction of the reaction fluid is preferably vertically downward.

In a case of carrying out esterification by filling the fixed bed type reactor with an ion exchange resin, the flow-through amount of the raw material including methacrylic acid and methanol is preferably 0.10 times or more and more preferably 0.20 times or more in terms of the mass ratio to the amount of the ion exchange resin. In addition, the flow-through amount of the raw material is preferably 10.0 times or less and more preferably 5.0 times or less in terms of the mass ratio with respect to the amount of the ion exchange resin. The above-described upper and lower limits may be combined in any combination. For example, the flow-through amount of the raw material including methacrylic acid and methanol is preferably 0.10 times or more and 10.0 times or less, more preferably 0.20 times or more and 10.0 times or less, and still more preferably 0.20 times or more and 5.0 times or less, in terms of the mass ratio to the amount of ion exchange resin.

When a strongly acidic cation exchange resin is used as the acid catalyst, the reaction temperature of the esterification is preferably 40° C. or higher and 130° C. or lower.

When the reaction temperature is 40° C. or higher, the reaction rate is high, and esterification can be carried out efficiently.

When the reaction temperature is 130° C. or lower, the deterioration rate of the ion exchange resin is low, and the esterification can be continuously carried out for a long time. The reaction temperature for esterification can be appropriately determined to the optimum temperature from the viewpoint of chemical equilibrium.

Regarding the raw material composition, from the viewpoint of chemical equilibrium, the process of the recovery step and the purification step can be simplified by increasing the concentration of any one of methacrylic acid or methanol and increasing the conversion rate of the raw material thereof having the lower concentration.

EXAMPLES

Hereinafter, the present invention will be specifically described with reference to Examples; however, the present invention is not limited to the following description.

The analysis of the raw material gas and the product was carried out using gas chromatography. The isobutanol conversion rate and the selectivity for each product are defined as follows.

Isobutanol conversion rate (%)=(b/a)×100
C4 gas selectivity (%)=(j/b)×100
Diisobutyl ether selectivity (%)=(h/b)×2×100
Isobutyl aldehyde selectivity (%)=(i/b)×100
Isobutylene selectivity in C4 gas (%)=(c/j)×100
Isobutane selectivity in C4 gas (%)=(d/j)×100
1-butene selectivity in C4 gas (%)=(e/j)×100
Trans-2-butene selectivity in C4 gas (%)=(f/j)×100
Cis-2-butene selectivity in C4 gas (%)=(g/j)×100
a: Number of moles of isobutanol supplied
b: Number of moles of isobutanol reacted
c: Number of moles of isobutylene generated
d: Number of moles of isobutane generated
e: Number of moles of 1-butene generated
f: Number of moles of trans-2-butene generated
g: Number of moles of cis-2-butene generated
h: Number of moles of diisobutyl ether generated
i: Number of moles of isobutyl aldehyde generated
j: Number of moles of C4 gas generated (isobutene, isobutane, 1-butene, trans-2-butene, and cis-2-butene)

The weight hourly space velocity (WHSV) per unit time of the raw material gas is defined by the following Expression (3).

$$WHSV(h^{-1})=W1/W2 \qquad (3)$$

However, in Expression (3), W1 is the supply amount (g/h) of isobutanol per unit time. W2 is the amount (g) of the catalyst used.

The flow rate and linear velocity of the raw material gas that is supplied to the catalyst layer are defined as follows. It is noted that the following raw material gas flow rate (L/h) is the total flow rate of the mixed gas consisting of the raw material isobutanol and the diluent gas.

Raw material gas flow rate (L/h)=Raw material gas flow rate (NL/h) measured in standard state×101.3 (kPa)/reaction pressure (kPa)×reaction temperature (K)/273 (K)

Linear velocity of raw material gas (cm/s)=raw material gas flow rate (L/h)×1,000/3,600/cross-sectional area of reaction tube (cm²)

[Reference Example]

A vertical-type tubular-shaped reaction tube having an inner diameter of 0.75 cm and a length of 40 cm was filled with 0.192 g of a dehydration catalyst (columnar pellet-shaped, crushed alumina molded to a diameter of 3.0 nm, alumina having a γ-alumina phase as the main component of the crystal phase, particle diameter: 800 to 1,190 μm, BET specific surface area: 243 m²/g, Na₂O content: less than 0.0500% by mass, SiO₂ content: less than 0.100% by mass, hereinafter referred to as the "catalyst A") to form a catalyst layer. For the reactor, the set temperature of the electric furnace for the reaction tube was adjusted so that the catalyst layer temperature became a predetermined temperature. In addition, the reaction pressure was adjusted using a back pressure valve so that the reaction pressure became a predetermined pressure. Next, isobutanol (manufactured by Nacalai Tesque, Inc., the amount of water measured according to the Karl Fischer method: 411 ppm) was introduced into a vaporizer heated at 200° C. at 0.263 ml/min with a double plunger pump and then vaporized. Nitrogen gas as a diluent gas was supplied to the vaporizer at a flow rate of 16 ml (standard state)/min using a mass flow meter, where it was supplied to the reactor together with the vaporized isobutanol. The isobutanol concentration in the raw material gas supplied to the catalyst layer was 79.9% by volume, and the temperature (the reaction temperature) of the catalyst layer during the reaction was 340° C.

The reaction evaluation was started 5 minutes after the variation of each of the catalyst layer temperature and the reaction pressure became stable within a predetermined temperature ±0.5° C. and a predetermined pressure ±0.5 kPa. After the reaction reached a steady state, the gas on the outlet side of the reactor was sampled and subjected to gas chromatography (manufactured by Shimadzu Corporation, GC-8A) to quantify isobutylene, isobutane, 1-butene, cis-2-butene, and trans-2-butene. In addition, the reaction gas discharged from the outlet side of the reactor was trapped in ice-cooled acetonitrile, and subjected to gas chromatography (manufactured by Shimadzu Corporation, GC-2014) to quantify unreacted isobutanol, diisobutyl ether, and isobutyl aldehyde. A pressure gauge for measuring the reaction pressure was installed between the vaporizer and the reactor inlet. It is noted that it was confirmed that the pressure loss from the vaporizer to the reactor inlet is negligibly small in all the flow rate ranges under the conditions in Examples 1 to 19 and Comparative Examples 1 to 6, including the present reference example. The measurement results of the isobutanol conversion rate at each reaction pressure, the selectivity for C4 gas (isobutylene, isobutane, 1-butene, cis-2-butene, trans-2-butene) in the product, and the isobutylene selectivity in the C4 gas are shown in Table 1 and FIG. 1.

TABLE 1

| Reaction pressure [kPa] | | 109 | 200 | 300 | 400 | 600 |
|---|---|---|---|---|---|---|
| Conversion rate of isobutyl alcohol [%] | | 74.3 | 72.8 | 62.8 | 60.7 | 55.9 |
| Selectivity [%] | Butenes | 98.8 | 98.2 | 96.6 | 96.2 | 94.7 |
| | Isobutane | 0.1 | 0.2 | 0.2 | 0.2 | 0.3 |
| | Diisobutyl ether | 1.0 | 1.6 | 3.1 | 3.5 | 4.9 |
| | Isobutyl aldehyde | 0.1 | 0.1 | 0.1 | 0.1 | 0.1 |
| Selectivity in C4 gas [%] | Isobutylene | 94.6 | 95.0 | 95.2 | 95.2 | 95.6 |
| | Isobutane | 0.1 | 0.2 | 0.2 | 0.2 | 0.2 |
| | 1-butene | 2.1 | 2.0 | 1.9 | 1.7 | 1.8 |
| | cis-2-butene | 2.5 | 2.3 | 2.2 | 2.4 | 1.9 |
| | trans-2-butene | 0.7 | 0.5 | 0.5 | 0.5 | 0.5 |

As shown in Table 1 and FIG. 1, when the reaction pressure is high, the conversion rate of isobutyl alcohol tends to decrease.

Example 1

Figure 2:
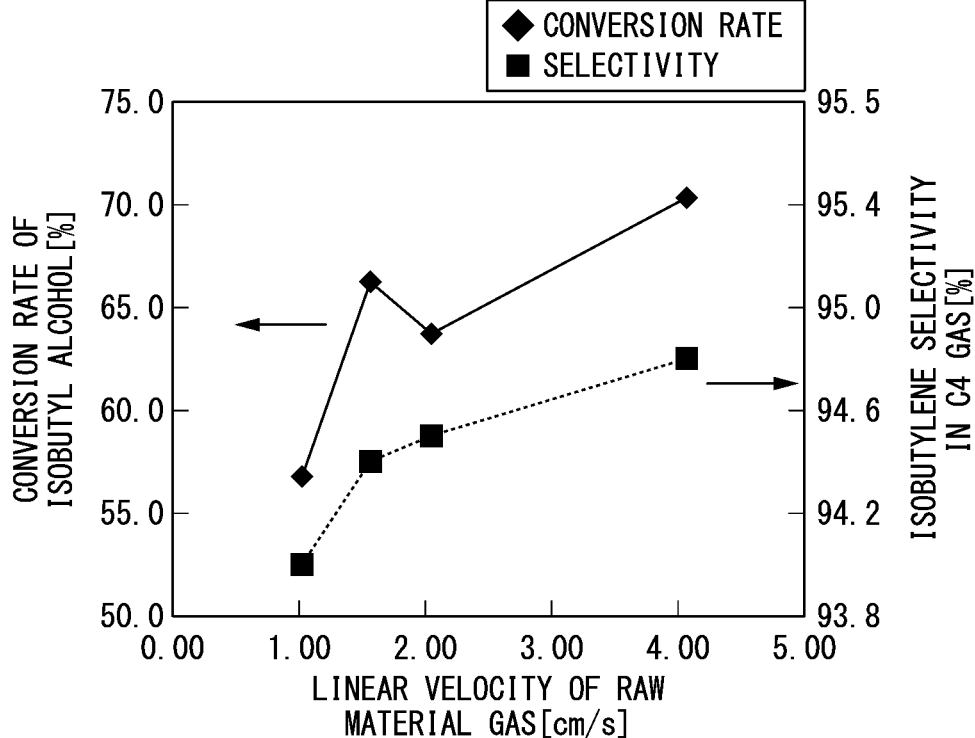
FIG. 2 is a graph showing the measurement results of the isobutanol conversion rate and the isobutylene selectivity in the C4 gas in Examples 1 to 3 and Comparative Example 1.

A vertical-type tubular-shaped reaction tube having an inner diameter of 1.0 cm and a length of 40 cm was filled with 0.232 g of crushed alumina (alumina consisting of crystal phases of γ-, θ-, α-alumina phases, particle diameter: 800 to 1,190 μm, BET specific surface area: 105 m²/g, Na₂O content: less than 0.0500% by mass, SiO₂ content: 0.160% by mass, hereinafter referred to as the "catalyst B") molded in a columnar pellet shape (diameter: 3.00 mm), as a catalyst for dehydration, and the reaction temperature and reaction pressure were each kept at 340° C. and 250 kPa. Next, the raw material gas consisting of isobutanol (the concentration in the raw material gas: 49.8% by volume) and nitrogen was supplied to a fixed bed reactor filled with 0.232 g of the catalyst B so that the linear velocity was 1.57 cm/s and isobutanol was brought into contact with alumina to obtain a product. The raw material gas flow rate was 2.50 L/h, and the WHSV was 19.5 h⁻¹. FIG. 2 and FIG. 2 show the measurement results of the isobutanol conversion rate, the C4 gas selectivity in the product, and the isobutylene selectivity in the C4 gas.

Examples 2 and 3 and Comparative Example 1

Products were obtained in the same manner as in Example 1 except that the reaction conditions were changed as shown in Table 2.

FIG. 2 and FIG. 2 show the measurement results of the isobutanol conversion rate, the C4 gas selectivity in the product, and the isobutylene selectivity in the C4 gas.

TABLE 2

| | | Example 1 | Example 2 | Example 3 | Comparative Example 1 |
|---|---|---|---|---|---|
| Catalyst | | B | B | B | B |
| Catalyst amount [g] | | 0.232 | 0.303 | 0.601 | 0.150 |
| Raw material gas | Isobutyl alcohol | 49.8 | 49.8 | 50.3 | 50.0 |
| [% by volume] | Nitrogen | 50.2 | 50.2 | 49.7 | 50.0 |
| Reaction pressure [kPa] | | 250 | 250 | 250 | 250 |
| Reaction temperature [° C.] | | 340 | 340 | 339 | 340 |
| WHSV [/h] | | 19.5 | 19.5 | 19.7 | 19.8 |
| Flow rate of raw material gas [L/h] | | 2.50 | 3.27 | 6.47 | 1.64 |
| Linear velocity of raw material gas [cm/s] | | 1.57 | 2.05 | 4.07 | 1.03 |
| Conversion rate of isobutyl alcohol [%] | | 66.2 | 63.7 | 70.3 | 56.8 |
| Selectivity [%] | Butenes | 96.5 | 95.7 | 96.1 | 96.7 |
| | Isobutane | 0.0 | 0.0 | 0.1 | 0.2 |
| | Diisobutyl ether | 3.5 | 4.2 | 3.7 | 2.9 |
| | Isobutyl aldehyde | 0.0 | 0.1 | 0.1 | 0.2 |
| | Isobutylene | 94.4 | 94.5 | 94.8 | 94.0 |
| Selectivity in C4 | Isobutane | 0.0 | 0.0 | 0.1 | 0.2 |
| gas [%] | 1-butene | 2.4 | 2.3 | 2.2 | 2.4 |
| | cis-2-butene | 2.6 | 2.5 | 2.3 | 2.6 |
| | trans-2-butene | 0.7 | 0.7 | 0.7 | 0.8 |

As shown in Table 2 and FIG. 2, in a case of being under the same pressure conditions, the higher the linear velocity of the raw material gas is, the higher the isobutanol conversion rate and the isobutylene selectivity are. In Examples 1 to 3 in which the linear velocity and the reaction pressure of the raw material gas are properly controlled, it is possible to produce isobutylene with a high selectivity while suppressing a decrease in the isobutanol conversion rate as compared with Comparative Example 1.

Example 4

A fixed bed reactor was filled with 0.232 g of the catalyst A and kept at 340° C. and 400 kPa. Next, the raw material gas consisting of isobutanol (the concentration in the raw material gas: 80.3% by volume) and nitrogen was supplied to a fixed bed reactor filled with 0.232 g of the catalyst A so that the linear velocity was 2.07 cm/s and isobutanol was brought into contact with alumina to obtain a product. The raw material gas flow rate was 3.29 L/h, and the WHSV was 66.3 h$^{-1}$. Table 3 and FIG. 3 show the measurement results of the isobutanol conversion rate, the C4 gas selectivity in the product, and the isobutylene selectivity in the C4 gas.

Examples 5 and 6 and Comparative Example 2

Products were obtained in the same manner as in Example 4 except that the reaction conditions were changed as shown in Table 3.

Figure 3:
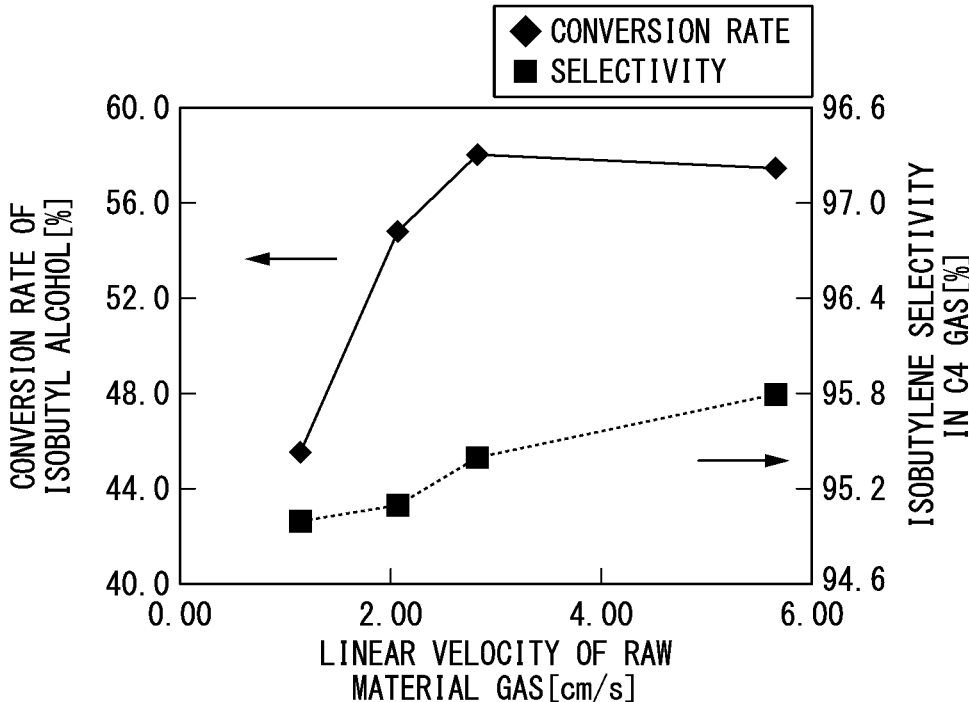
FIG. 3 is a graph showing the measurement results of the isobutanol conversion rate and the isobutylene selectivity in the C4 gas in Examples 4 to 6 and Comparative Example 2.

Table 3 and FIG. 3 show the measurement results of the isobutanol conversion rate, the C4 gas selectivity in the product, and the isobutylene selectivity in the C4 gas.

TABLE 3

| | | Example 4 | Example 5 | Example 6 | Comparative Example 2 |
|---|---|---|---|---|---|
| Catalyst | | A | A | A | A |
| Catalyst amount [g] | | 0.232 | 0.325 | 0.653 | 0.131 |
| Raw material gas | Isobutyl alcohol | 80.3 | 79.5 | 79.5 | 79.4 |
| [% by volume] | Nitrogen | 19.7 | 20.5 | 20.5 | 20.6 |
| Reaction pressure [kPa] | | 400 | 400 | 400 | 400 |
| Reaction temperature [° C.] | | 340 | 340 | 340 | 340 |
| WHSV [/h] | | 66.3 | 63.9 | 63.7 | 64.3 |
| Flow rate of raw material gas [L/h] | | 3.29 | 4.49 | 8.99 | 1.83 |
| Linear velocity of raw material gas [cm/s] | | 2.07 | 2.83 | 5.66 | 1.15 |
| Conversion rate of isobutyl alcohol [%] | | 54.8 | 58.0 | 57.5 | 45.6 |
| Selectivity [%] | Butenes | 92.7 | 94.2 | 93.4 | 91.1 |
| | Isobutane | 0.2 | 0.3 | 0.2 | 0.4 |
| | Diisobutyl ether | 6.9 | 5.3 | 6.2 | 8.0 |
| | Isobutyl aldehyde | 0.2 | 0.2 | 0.2 | 0.5 |
| Selectivity in C4 | Isobutylene | 95.1 | 95.4 | 95.8 | 95.0 |
| gas [%] | Isobutane | 0.3 | 0.3 | 0.2 | 0.5 |
| | 1-butene | 2.1 | 2.0 | 1.9 | 2.1 |
| | cis-2-butene | 2.0 | 1.8 | 1.6 | 1.8 |
| | trans-2-butene | 0.5 | 0.5 | 0.5 | 0.6 |

15

16

As shown in Table 3 and FIG. 3, in a case of being under the same pressure conditions, the higher the linear velocity of the raw material gas is, the higher the isobutanol conversion rate and the isobutylene selectivity are. In Examples 4 to 6 in which the linear velocity and the reaction pressure of the raw material gas are properly controlled, it is possible to produce isobutylene with a high selectivity while suppressing a decrease in the isobutanol conversion rate as compared with Comparative Example 2.

Example 7

A fixed bed reactor was filled with 0.132 g of the catalyst A and kept at 340° C. and 200 kPa. Next, the raw material gas consisting of isobutanol (the concentration in the raw material gas: 79.4% by volume) and nitrogen was supplied to a fixed bed reactor filled with 0.132 g of the catalyst A so that the linear velocity was 4.57 cm/s and isobutanol was brought into contact with alumina to obtain a product. The raw material gas flow rate was 7.27 L/h, and the WHSV was 127 h$^{-1}$. Table 4 and FIG. 4 show the measurement results of the isobutanol conversion rate, the C4 gas selectivity in the product, and the isobutylene selectivity in the C4 gas.

Examples 8 and 9 and Comparative Example 3

Products were obtained in the same manner as in Example 7 except that the reaction conditions were changed as shown in Table 4.

Figure 4:
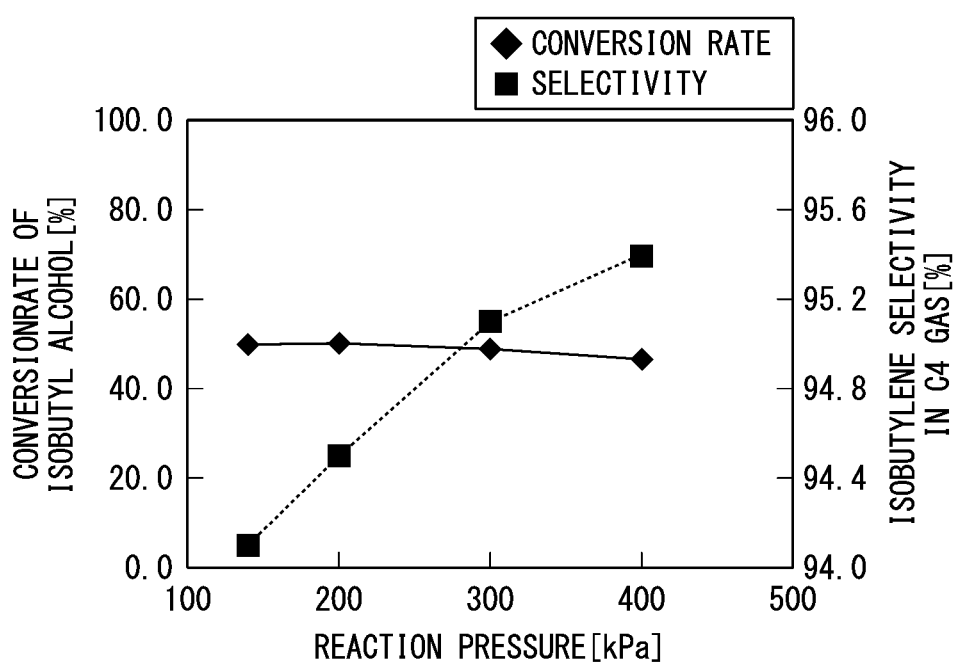
FIG. 4 is a graph showing the measurement results of the isobutanol conversion rate and the isobutylene selectivity in the C4 gas in Examples 7 to 9 and Comparative Example 3.

Table 4 and FIG. 4 show the measurement results of the isobutanol conversion rate, the C4 gas selectivity in the product, and the isobutylene selectivity in the C4 gas.

TABLE 4

|  |  | Example 7 | Example 8 | Example 9 | Comparative Example 3 |
|---|---|---|---|---|---|
| Catalyst |  | A | A | A | A |
| Catalyst amount [g] |  | 0.132 | 0.193 | 0.268 | 0.091 |
| Raw material gas | Isobutyl alcohol | 79.4 | 79.6 | 79.9 | 79.6 |
| [% by volume] | Nitrogen | 20.6 | 20.4 | 20.1 | 20.4 |
| Reaction pressure [kPa] |  | 200 | 300 | 400 | 140 |
| Reaction temperature [° C.] |  | 340 | 340 | 340 | 340 |
| WHSV [/h] |  | 127 | 129 | 127 | 128 |
| Flow rate of raw material gas [L/h] |  | 7.27 | 7.13 | 7.32 | 7.19 |
| Linear velocity of raw material gas [cm/s] |  | 4.57 | 4.48 | 4.60 | 4.52 |
| Conversion rate of isobutyl alcohol [%] |  | 50.1 | 48.8 | 46.5 | 49.8 |
| Selectivity [%] | Butenes | 94.4 | 93.5 | 91.5 | 95.9 |
|  | Isobutane | 0.2 | 0.2 | 0.2 | 0.2 |
|  | Diisobutyl ether | 5.2 | 6.1 | 8.0 | 3.6 |
|  | Isobutyl aldehyde | 0.2 | 0.2 | 0.3 | 0.3 |
| Selectivity in C4 | Isobutylene | 94.5 | 95.1 | 95.4 | 94.1 |
| gas [%] | Isobutane | 0.3 | 0.2 | 0.2 | 0.2 |
|  | 1-butene | 2.4 | 2.2 | 2.1 | 2.5 |
|  | cis-2-butene | 2.2 | 2.0 | 1.8 | 2.5 |
|  | trans-2-butene | 0.6 | 0.5 | 0.5 | 0.7 |

As shown in Table 4 and FIG. 4, in Examples 7 to 9 in which the linear velocity and the reaction pressure of the raw material gas are properly controlled, it is possible to produce isobutylene with a high selectivity at the same reaction temperature while suppressing a decrease in the isobutanol conversion rate as compared with Comparative Example 3.

Example 10

Figure 5:
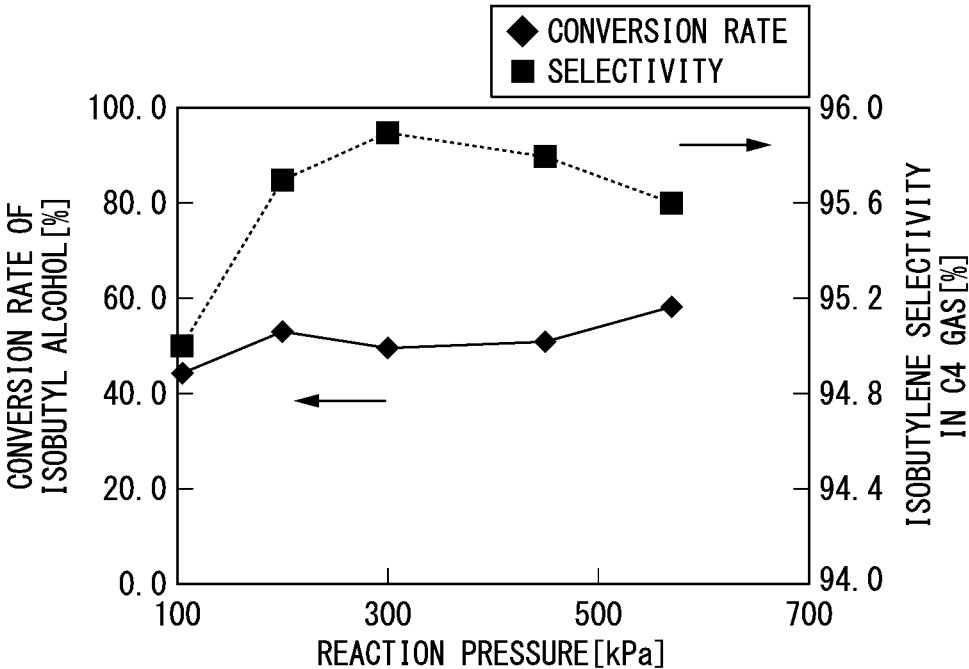
FIG. 5 is a graph showing the measurement results of the isobutanol conversion rate and the isobutylene selectivity in the C4 gas in Examples 10 to 13 and Comparative Example 4.

A fixed bed reactor was filled with 0.591 g of the catalyst B and kept at 340° C. and 200 kPa. Next, the raw material gas consisting of isobutanol (the concentration in the raw material gas: 80.1% by volume) and nitrogen was supplied to a fixed bed reactor so that the linear velocity was 4.53 cm/s and isobutanol was brought into contact with alumina to obtain a product. The raw material gas flow rate was 7.21 L/h, and the WHSV was 28.4 h$^{-1}$. Table 5 and FIG. 5 show the measurement results of the isobutanol conversion rate, the C4 gas selectivity in the product, and the isobutylene selectivity in the C4 gas.

Examples 11 to 13 and Comparative Example 4

Products were obtained in the same manner as in Example 10 except that the reaction conditions were changed as shown in Table 5. Table 5 and FIG. 5 show the measurement results of the isobutanol conversion rate, the C4 gas selectivity in the product, and the isobutylene selectivity in the C4 gas.

TABLE 5

|  |  | Example 10 | Example 11 | Example 12 | Example 13 | Comparative Example 4 |
|---|---|---|---|---|---|---|
| Catalyst |  | B | B | B | B | B |
| Catalyst amount [g] |  | 0.591 | 0.891 | 1.204 | 1.652 | 0.302 |
| Raw material gas | Isobutyl alcohol | 80.1 | 79.9 | 80.0 | 79.9 | 79.9 |
| [% by volume] | Nitrogen | 19.9 | 20.1 | 20.0 | 20.1 | 20.1 |
| Reaction pressure [kPa] |  | 200 | 300 | 450 | 570 | 105 |
| Reaction temperature [° C.] |  | 340 | 340 | 340 | 338 | 340 |
| WHSV [/h] |  | 28.4 | 28.4 | 28.3 | 28.7 | 28.7 |
| Flow rate of raw material gas [L/h] |  | 7.21 | 7.26 | 6.51 | 7.85 | 7.10 |
| Linear velocity of raw material gas [cm/s] |  | 4.53 | 4.56 | 4.09 | 4.94 | 4.47 |
| Conversion rate of isobutyl alcohol [%] |  | 53.0 | 49.6 | 51.0 | 58.3 | 44.3 |
| Selectivity [%] | Butenes | 93.2 | 91.3 | 91.1 | 91.6 | 94.3 |
|  | Isobutane | 0.1 | 0.1 | 0.1 | 0.2 | 0.1 |
|  | Diisobutyl ether | 6.5 | 8.4 | 4.4 | 8.0 | 5.5 |
|  | Isobutyl aldehyde | 0.1 | 0.2 | 0.2 | 0.2 | 0.1 |
| Selectivity in C4 | Isobutylene | 95.7 | 95.9 | 95.8 | 95.6 | 95.0 |
| gas [%] | Isobutane | 0.1 | 0.1 | 0.1 | 0.2 | 0.2 |
|  | 1-butene | 1.8 | 1.7 | 1.8 | 1.9 | 2.2 |
|  | cis-2-butene | 1.9 | 1.8 | 1.7 | 1.8 | 2.1 |
|  | trans-2-butene | 0.5 | 0.5 | 0.5 | 0.5 | 0.6 |

As shown in Table 5 and FIG. 5, in Examples 10 to 13 in which the linear velocity and the reaction pressure of the raw material gas are properly controlled, it is possible to produce isobutylene with a high selectivity while suppressing a decrease in conversion rate as compared with Comparative Example 4.

Example 14

Figure 6:
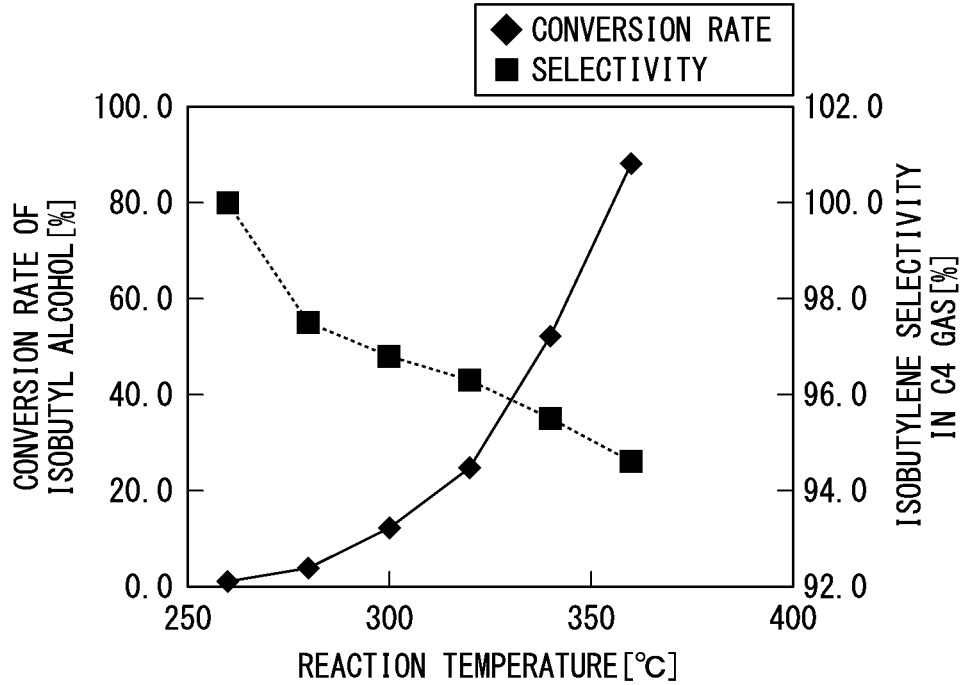
FIG. 6 is a graph showing the measurement results of the isobutanol conversion rate and the isobutylene selectivity in the C4 gas in Examples 14 to 19.

A fixed bed reactor was filled with 0.903 g of the catalyst B and kept at 360° C. and 450 kPa. Next, the raw material gas consisting of isobutanol (the concentration in the raw material gas: 79.9% by volume) and nitrogen was supplied to a fixed bed reactor filled with 0.903 g of the catalyst B so that the linear velocity was 1.57 cm/s and isobutanol was brought into contact with alumina to obtain a product. The raw material gas flow rate was 2.50 L/h, and the WHSV was 14.0 h$^{-1}$. Table 6 and FIG. 6 show the measurement results of the isobutanol conversion rate, the C4 gas selectivity in the product, and the isobutylene selectivity in the C4 gas.

Examples 15 to 19

Products were obtained in the same manner as in Example 14 except that the reaction conditions were changed as shown in Table 5. Table 6 and FIG. 6 show the measurement results of the isobutanol conversion rate, the C4 gas selectivity in the product, and the isobutylene selectivity in the C4 gas.

TABLE 6

|  |  | Example 14 | Example 15 | Example 16 | Example 17 | Example 18 | Example 19 |
|---|---|---|---|---|---|---|---|
| Catalyst |  | B | B | B | B | B | B |
| Catalyst amount [g] |  | 0.903 | 0.903 | 0.903 | 0.903 | 0.901 | 0.903 |
| Raw material gas | Isobutyl alcohol | 79.9 | 79.9 | 79.9 | 79.9 | 79.9 | 79.9 |
| [% by volume] | Nitrogen | 20.1 | 20.1 | 20.1 | 20.1 | 20.1 | 20.1 |
| Reaction pressure [kPa] |  | 450 | 450 | 450 | 450 | 450 | 450 |
| Reaction temperature [° C.] |  | 360 | 340 | 320 | 300 | 280 | 260 |
| WHSV [/h] |  | 14.0 | 14.0 | 14.0 | 14.0 | 14.0 | 14.0 |
| Flow rate of raw material gas [L/h] |  | 2.50 | 2.42 | 2.34 | 2.26 | 2.18 | 2.10 |
| Linear velocity of raw material gas [cm/s] |  | 1.57 | 1.52 | 1.47 | 1.42 | 1.37 | 1.32 |
| Conversion rate of isobutyl alcohol [%] |  | 88.1 | 52.2 | 24.7 | 12.2 | 3.8 | 1.0 |
| Selectivity [%] | Butenes | 97.6 | 88.4 | 81.2 | 79.9 | 69.6 | 54.8 |
|  | Isobutane | 0.2 | 0.1 | 0.1 | 0.2 | 0.2 | 0.0 |
|  | Diisobutyl ether | 2.1 | 11.3 | 18.5 | 19.6 | 30.2 | 45.2 |
|  | Isobutyl aldehyde | 0.1 | 0.2 | 0.2 | 0.3 | 0.0 | 0.0 |
| Selectivity in C4 | Isobutylene | 94.6 | 95.5 | 96.3 | 96.8 | 97.5 | 100.0 |
| gas [%] | Isobutane | 0.2 | 0.2 | 0.2 | 0.2 | 0.2 | 0.0 |
|  | 1-butene | 2.2 | 1.9 | 1.6 | 1.3 | 1.1 | 0.0 |
|  | cis-2-butene | 2.3 | 1.9 | 1.5 | 1.3 | 0.9 | 0.0 |
|  | trans-2-butene | 0.7 | 0.5 | 0.4 | 0.4 | 0.3 | 0.0 |

As shown in Table 6 and FIG. 6, the higher the reaction temperature, the higher the conversion rate, and the lower the reaction temperature, the higher the isobutylene selectivity.

Examples 20 and 21

Products were obtained in the same manner as in Example 3 except that the reaction conditions were changed as shown in Table 7. Table 7 and FIG. 7 show the measurement results of the isobutanol conversion rate, the C4 gas selectivity in the product, and the isobutylene selectivity in the C4 gas.

TABLE 7

| | | Example 20 | Example 21 |
|---|---|---|---|
| Catalyst | | B | B |
| Catalyst amount [g] | | 0.601 | 0.902 |
| Raw material gas | Isobutyl alcohol | 50.1 | 79.9 |
| [% by volume] | Nitrogen | 49.9 | 20.1 |
| Reaction pressure [kPa] | | 250 | 250 |
| Reaction temperature [° C.] | | 339 | 340 |
| WHSV [/h] | | 14.6 | 14.0 |
| Flow rate of raw material gas [L/h] | | 5.29 | 4.78 |
| Linear velocity of raw material gas [cm/s] | | 3.02 | 2.74 |
| Conversion rale of isobutyl alcohol [%] | | 82.7 | 67.6 |
| Selectivity [%] | Butenes | 97.7 | 93.9 |
| | Isobutane | 0.1 | 0.1 |
| | Diisobutyl ether | 2.0 | 5.8 |
| | Isobutyl aldehyde | 0.1 | 0.2 |
| Selectivity in C4 | Isobutylene | 94.4 | 95.3 |
| gas [%] | Isobutane | 0.2 | 0.2 |
| | 1-butene | 2.2 | 1.9 |
| | cis-2-butene | 2.4 | 2.1 |
| | trans-2-butene | 0.8 | 0.6 |

Figure 7:
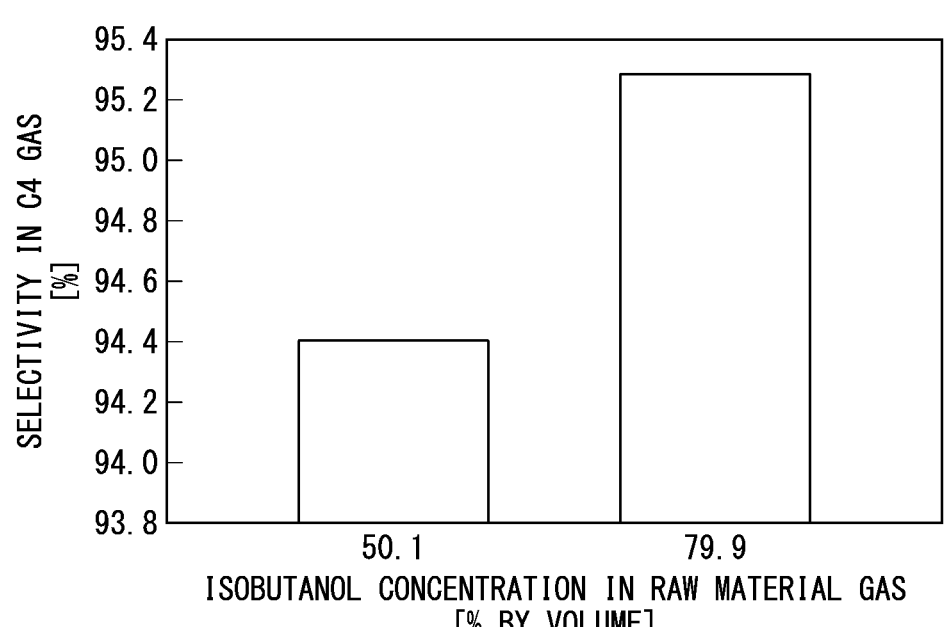
FIG. 7 is a graph showing the measurement result of the isobutylene selectivity in the C4 gas in Examples 20 and 21.

As shown in Table 7 and FIG. 7, the higher the reaction temperature, the higher the conversion rate, and the lower the reaction temperature, the higher the isobutylene selectivity.

What is claimed is:

1. A method for producing isobutylene, in which a raw material gas containing isobutanol is brought into contact with a catalyst to produce isobutylene from isobutanol, the method comprising: bringing the raw material gas containing isobutanol into contact with a catalyst at a linear velocity of 1.20 cm/s or more under a pressure of 120 kPa or more in terms of absolute pressure to produce isobutylene from isobutanol.

2. The method for producing isobutylene according to claim 1, wherein a concentration of the isobutanol contained in the raw material gas containing isobutanol is 15% by volume or more and 100% by volume or less.

3. The method for producing isobutylene according to claim 1, wherein the catalyst has a particle diameter of 700 μm or more and 10,000 μm or less.

4. The method for producing isobutylene according to claim 1, wherein the catalyst is a catalyst containing alumina.

5. A method for producing methacrylic acid, comprising:
producing isobutylene according to the method of claim 1, and
producing methacrylic acid from the isobutylene.

6. A method for producing methacrylic acid, comprising:
producing isobutylene according to the method of claim 1,
producing tert-butyl alcohol from the isobutylene, and
producing methacrylic acid from the tert-butyl alcohol.

7. A method for producing methyl methacrylate, comprising:
producing methacrylic acid according to the method of claim 5, and
producing methyl methacrylate from the methacrylic acid.

* * * * *